United States Patent [19]
Cheng et al.

[11] Patent Number: 5,965,605
[45] Date of Patent: Oct. 12, 1999

[54] INHIBITION OF THE BINDING HUMAN IGE TO ITS RECEPTOR BY TETRACYCLIC COMPOUNDS FOR THE ALLEVIATION OF IGE-MEDIATED IMMUNE RESPONSE

[75] Inventors: Y.-S. Edmond Cheng, Wayland; Yuan Liu, Lexington; John Chu, Belmont; Jean-Pierre Kinet, Lexington; Marie-Helene Jouvin, Brookline, all of Mass.; Yukio Sudo, Saitama, Japan; Xiuqi Qian, Concord, Mass.

[73] Assignee: Heska Corporation, Fort Collins, Colo.

[21] Appl. No.: 08/999,348

[22] Filed: Dec. 29, 1997

Related U.S. Application Data

[63] Continuation of application No. 08/698,243, Aug. 15, 1996, abandoned, which is a continuation-in-part of application No. 08/635,372, Apr. 19, 1996, abandoned.

[51] Int. Cl.$^6$ .................................................. A61K 31/35
[52] U.S. Cl. .......................... 514/454; 549/388; 514/337
[58] Field of Search ............................. 514/454; 549/388

[56] References Cited

U.S. PATENT DOCUMENTS 4,318,846  3/1982  Khanna et al. ........................ 435/188

FOREIGN PATENT DOCUMENTS

| 0 025 912 A1 | 4/1981 | European Pat. Off. . |
| 0 224 120 A2 | 6/1987 | European Pat. Off. . |
| 27 16 515 A1 | 10/1977 | Germany . |
| WO 94/05688 | 3/1994 | WIPO . |
| WO 95/02324 | 1/1995 | WIPO . |
| WO 95/16026 | 6/1995 | WIPO . |

OTHER PUBLICATIONS

Adamczewski et al., "The High–Affinity Receptor for Immunoglobulin E," *Chem. Immunol.*, 50:173–190 (1994).

Blank et al., "Characterization of Truncated α Chain Products from Human, Rat, and Mouse High Affinity Receptor for Immunoglobulin E," *J. of Biological Chemistry*, 266: No. 4, 2639–2646 (1991).

Haak–Frendscho et al., "Human IgE Receptor α–Chain IgG Chimera Blocks Passive Cutaneous Anaphylaxis Reaction in Vivo," *J. of Immunology*, 151: No. 1, 351–358 (1993).

Hakimi et al., "The α Subunit of the Human IgE Receptor (FcERI) Is Sufficient for High Affinity IgE Binding," *J. of Biological Chemistry*, 265: No. 36, 22079–22081 (1990).

Nio et al., "Inhibition of Passive Sensitization of Human Peripheral Basophils by Synthetic Human Immunoglobulin E Peptide Fragments," *Federation of European Biochemical Societies (FEBS)*, 319: No. 3, 225–228 (1993).

Scharenberg et al., "Early Events in Mast Cell Signal Transduction," *Chemical Immunology*, 61:72–87 (1995).

Shearer et al., "The Immune System An Overview," *Allergy Principles and Practice, Fourth Edition*, pp. 3–21.

Orndorff et al., "Tetrachloroflourescein and Some of its Derivatives", *J. Amer. Chem. Soc.*, 36:680–725 (Feb. 10, 1914).

M. Tanaka et al. "Dehydrate Wirkung Von Japanischer Saureerde In Anthrachinonreihe", *Bulletin of the Chemical Society of Japan*, 3:288–289 (Sep. 24, 1928).

Lamberts et al., "Rose Bengal and Nonpolar Derivatives", *J. Am. Chem. Soc.*, 105:7465–7467 (1983).

Zakrzewski et al., "The Bleaching Behavior of Rose Bengal Under Reducing Conditions Has Been Elucidated by Determining the Products of Chemical and Photochemical Reduction of Rose Bengal", *Tetrahedron*, 43 (No. 20):4507–4512 (1987).

Packard et al., "Site–Directed Labeling of a Monoclonal Antibody: Targeting to a Disulfide Bond", *Biochemistry*, 25:3548–3552 (1986).

CA 90:33490, Vrbsky et al., 1979.
CA 82: 179906, Antonovich et al., 1975.
Beilstein Reg. No. 367004.
Beilstein Reg. No. 855444.

*Primary Examiner*—Jane Fan
*Attorney, Agent, or Firm*—Heska Corporation

[57] ABSTRACT

Disclosed are chemical agents with unexpected activity to inhibit the interactions between human immunoglobulin E (IgE) and its receptor (FcεRI) which interactions are known to be involved in triggering allergic responses. The agents may be used to module the allergic response in the treatment of various clinical conditions, including rhinitis, asthma, urticaria, atopic dermatitis, and anaphylacric shock. The agents can be formulated for oral, topical or parenteral administration.

24 Claims, No Drawings

INHIBITION OF THE BINDING HUMAN IGE TO ITS RECEPTOR BY TETRACYCLIC COMPOUNDS FOR THE ALLEVIATION OF IGE-MEDIATED IMMUNE RESPONSE

CROSS REFERENCE TO RELATED APPLICATIONS

This application is a continuation of U.S. application Ser. No. 08/698,243, filed Aug. 15, 1996, entitled "Inhibition of the binding of human IgE to its receptor by tetracyclic compounds for the alleviation of IgE-Mediated immune response" now abandoned which is a continuation-in-part of U.S. application Ser. No. 08/635,372, filed Apr. 19, 1996, now abandoned.

BACKGROUND OF THE INVENTION

Some allergic individuals produce antibodies from a particular class of immunoglobulin called IgE against harmless allergens (Shearer, W. T. and Huston, D. P., Allergy, Principles and Practice, 1:15–17, 1993.) Most of the allergic reaction is the result of the interactions between IgE, the corresponding allergen that this particular IgE is specific for, and the high affinity IgE receptor, FcεRI. FcεRI is expressed at the surface of basophils in the blood and mast cells in solid tissues (Adamczewski, M. and Kinet, J-P, Chemical Immunology, 59:173–190, 1994.) When an allergen interacts with its specific IgE already bound to FcεRI on a cell, the cell is activated. This activation results in the production and release by the cell of allergy mediators, such as histamine, scrotonin, lipid mediators. The mechanism is responsible for a variety of clinical syndromes, including allergic rhinitis, asthma, atopic dermatitis, anaphylactic shock.

FcεRI is a tetrameric receptor composed of an IgE-binding α chain, a β chain and a dimer of γ chains (Adamczewski, M. and Kinet, J-P, Chemical Immunology, 59:173–190, 1994). Both the β and γ chains are responsible for generating cell-activating signals when an allergen binds to a receptor-bound IgE molecule (Scharenberg and Kinet, Human Basophils and Mast Cells; Biological Aspects, 61:72–87, 1995). The IgE binding site is located in the extracellular portion of the α chain (Hakimi et al., J. Biol. Chem., 265:3822079–22081, 1990, Blank et al., J. Biol. Chem. 266:2639–2646 1991), as shown by the binding of IgE to the soluble form of the α cabin, termed herein FcεRI α, comprising only its extracellular portion made by genetic engineering, with the same characteristics as the tetrameric FcεRI.

IgE-mediated reactions are responsible for many allergic diseases, such as rhinitis (hay fever), asthma, urticaria, and atopic dermatitis. Intervention at the level of IgE and FcεRI interaction may prevent the IgE mediated immune responses that lead to allergic disorders. Previously, other investigators have tried to produce competitive inhibitors using IgE peptide analogs (Noriki, et al., FEBS Let., 319:225–228, 1993). For example, human soluble FcεRI α-chain inhibited human IgE binding FcεRI on Chinese hamster ovary cells and blocked passive cutaneous anaphylaxis reaction in vivo (Haak-Frendscho, et al., J. Immunol., 151:351–358, 1993). However, peptides and proteins generally are difficult to be formulated into drugs because of their unfavorable bioavailability, Anti-IgE antibodies have been used to remove IgE from circulation for the treatment of IgE mediated allergies (Chang, et al., BioTechnology, 8:122–126, 1990). Although antibodies have longer half-lives than proteins, they will elicit immunologic responses, require intravenous injection, and they are expensive to manufacture. The third option to inhibit IgE mediated immune responses would be to use small chemical inhibitors that can block the interaction between IgE and FcεRI.

It is the object of this invention to provide chemical compositions for antagonizing the interaction between IgE and FcεRI. It is another object of this invention to provide a method for antagonizing the interaction between IgE and FcεRI in which the antagonization is effective to prevent IgE-mediated response, is effective to inhibit mediator release from cells, and is effective to block the anaphylactic reaction in vivo. It is still another object of the invention, to provide an in vitro diagnostic for measuring antibodies against FcεRI.

SUMMARY OF THE INVENTION

A class of compounds having a tetracyclic skeleton have been discovered to antagonize the interaction between immunoglobulin E ("IgE") and its high affinity receptor ("FcεRI"). The compounds also have been discovered to be therapeutically useful in alleviating IgE-mediated immune response to an allergen that leads to cellular release of allergy mediators, such as histamine, and in alleviating anaphylactic reactions in vivo.

In one aspect, the invention is embodied as a composition for antagonizing the interaction between IgE and FcεRI. The composition comprises a pharmaceutically acceptable carrier for oral, parenteral or topical application, and a IgE antagonizing amount of a compound having the following formula:

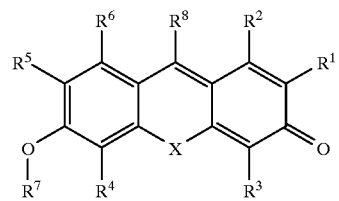

The atom or group represented by each of $R^1, R^2, R^3, R^4, R^5$, and $R^6$ is the same or different and is independently hydrogen, hydroxyl, nitro, cyano, isothiocyano, a halogen, a sulfo group, a phospho group, an alkyl group having 1 to 6 carbon atoms, an allyl group, an alkoxy group having 1 to 6 carbon atoms, an aryl group, a heteroaryl group, an alkylaryl group, an allylaryl group, an alkoxycarbonyl group has 1 to 6 carbon atoms, a carboxy group, an alkylcarbonyl group having 1 to 6 carbon atoms or where appropriate, salts thereof. The atom or group represented by each of $R^1, R^2, R^3, R^4, R^5$ and $R^6$ also independently can be an aminocarbonyl group, an alkylaminocarbonyl group having 1 to 6 carbon atoms, an arylaminocarbonyl group, a heteroarylaminocarbonyl group, an acylamino group, an alklylamino group having 1 to 6 carbon atoms, a dialkylamino group, an arylamino group, an alkylurea group having 1 to 6 carbon atoms, an arylurea group, an alkylsulfonyl group having 1 to 6 carbons atoms, an arylsulfonyl group, an alkylsulfonylamino group having 1 to 6 carbon atoms, an arylsulfonylamino group, or where appropriate, salts thereof.

The atom or group represent by $R^7$ is hydrogen, a pharmaceutically acceptable metal ion, an arylcarbonyl group or an alkylcarbonyl group having 1 to 6 carbon atoms. The variable X is oxygen, sulfur or a secondary or tertiary nitrogen moiety having the formula $NR^9$, where $R^9$ is hydrogen or an alkyl group having 1 to 6 carbon atoms. The group represented by $R^8$ is an aryl group or a heteroaryl group thereby providing the fourth ring of the tetracyclic skeleton of the compound. As used herein, the term "tetracyclic compound" generally refers to compounds of is invention.

The members of the above described class of compounds antagonize the bioding of IgE to FcεRI. As used herein, "antagonize" means to reduce, inhibit, or block the binding of IgE to its binding site upon the IgE receptor, FcεRI. The disclosure herein teaches those of ordinary skill in the art how to identify various individual compounds which effectively antagonize the IgE/FcεRI interaction sufficient to have significant therapeutic or diagnostic utility. The disclosure provided herein also teaches how to use compositions having activity that antagonizes the interaction between IgE and FcεRI.

In preferred embodiments of the tetracyclic compound, the variable X is oxygen. The atom or group represented by $R^1$ and $R^6$ is hydrogen and the atom or group represented by $R^1$, $R^3$, $R^4$, $R^5$ is hydrogen, hydroxyl, nitro, cyano or a halogen such as fluorine, chlorine, bromine or iodine. In other preferred embodiments, the atom represented by $R^7$ is hydrogen or a pharmaceutically acceptable metal ion.

In one preferred embodiment, the group represented by $R^8$ has the formula:

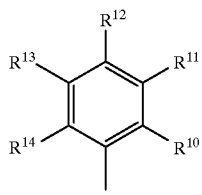

The atom or group represented by each of $R^{10}$, $R^{11}$, $R^{12}$, $R^{13}$ and $R^{14}$ is the same or different and is independently hydrogen, hydroxyl, nitro, cyano, isothiocyano, a halogen, an alkyl group having 1 to 6 carbon atoms, an allyl group, an alkoxycarbonyl group having 1 to 6 carbon atoms, an aryloxycabonyl group, a carboxy group, a sulfo group, a phospho group, or where appropriate, salts thereof. The atom or group represented by each of $R^{10}$, $R^{11}$, $R^{12}$, $R^{13}$ and $R^{14}$ also independently can be an alkylcarbonyl group having 1 to 6 carbon atoms, an arylcarbonyl group, an alkylsulfonyl group having 1 to 6 carbon atoms, an arylsulfonyl group, a sulfamoyl group, an alkylsulfamoyl group having 1 to 6 carbon atoms, an arylsulfamoyl group, an acylamino group having 1 to 6 carbon atoms or where appropriate, salts thereof.

In more preferred embodiments, the atom or group represented by $R^{10}$ is a carboxylic acid, a carboxylic ester or a pharmaceutically acceptable salt thereof. The entity $R^{10}$ can be represented by the formula $-CO_2R^{15}$. Accordingly, $R^{15}$ is hydrogen, a linear or branched alkyl group, an aryl group, a heteroaryl group or a pharmaceutically acceptable metal ion. In another more preferred embodiment, the atom or group represented by $R^{11}$, $R^{12}$, $R^{13}$ and $R^{14}$ independently hydrogen, isothiocyano, a halogen, a carboxylic ester, a carboxylic acid or pharmaceutically acceptable salts thereof.

In another more preferred embodiment, the variables $R^1$ and $R^5$ are the same and $R^3$ and $R^4$ are the same. In yet another preferred embodiment, the variables $R^1$, $R^3$, $R^4$ and $R^5$ are all the same. Other more preferred embodiments have the atom or group represented by $R^{11}$, $R^{12}$, $R^{13}$ and $R^{14}$ independently being hydrogen or a halogen.

More preferred embodiments of the invention have the following formulae:

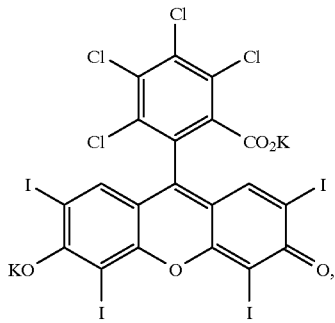

Compound 1

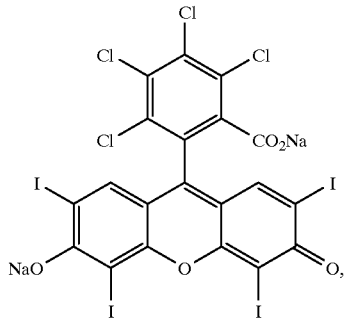

Compound 2

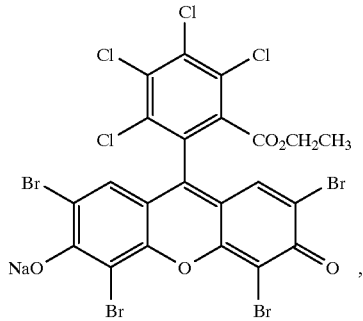

Compound 3

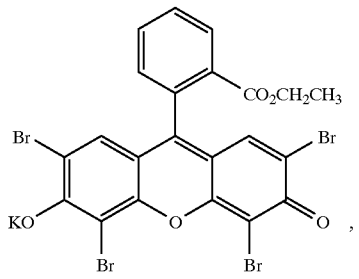

Compound 4

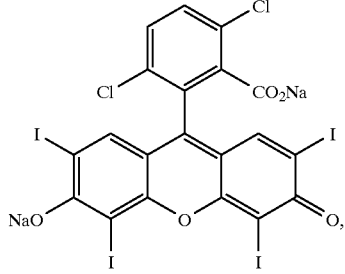

Compound 5

-continued

Compound 6

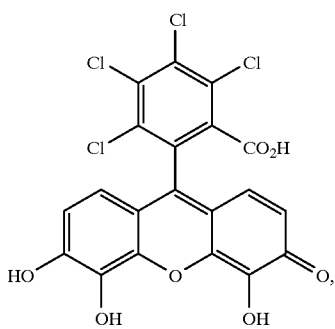

Compound 7

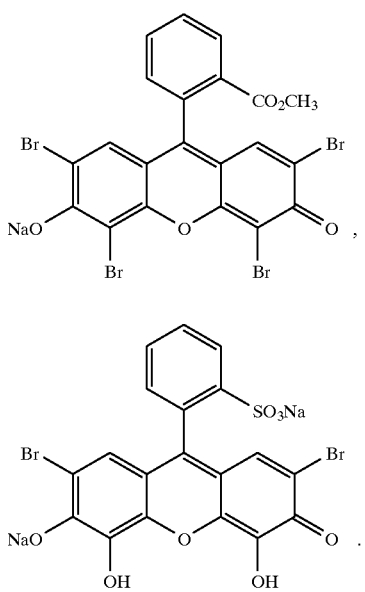
and

Compound 8

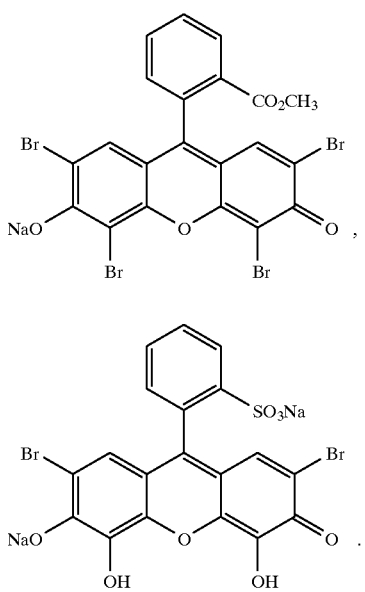

In another preferred embodiment, the group represented by $R^8$ has the formula:

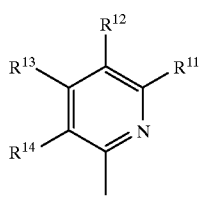

The atom or group represented by each of $R^{11}$, $R^{12}$, $R^{13}$ and $R^{14}$ is the same or different and is independently hydrogen, hydroxyl, nitro, cyano, isothiocyano, a halogen, an alkyl group having 1 to 6 carbon atoms, an allyl group, an alkoxycarbonyl group having 1 to 6 carbon atoms, an aryloxycarbonyl group, a carboxy group, a sulfo group, a phospho group, an alkylcarbonyl group having 1 to 6 carbon atoms, an arylcarbonyl group or where appropriate, salts thereof. The atom or group represented by each of $R^{11}$, $R^{12}$, $R^{13}$ and $R^{14}$ also independently can be an alkylsulfonyl group having 1 to 6 carbon atoms, an arylsulfonyl group, a sulfamoyl group, an alkylsulfamoyl group having 1 to 6 carbon atoms, an arylsulfamoyl group, an acylamino group having 1 to 6 carbon atoms or where appropriate, salts thereof.

In more preferred embodiments, the atom or group represented by $R^{11}$, $R^{12}$, $R^{13}$ and $R^{14}$ is independently hydrogen, a halogen, a carboxylic ester, a carboxylic acid or a pharmaceutically acceptable salt thereof. In another more preferred embodiment, the atom or group represented by $R^{11}$ or $R^{14}$ is the group $-CO_2R^{15}$ where $R^{15}$ represents hydrogen, a linear or branched alkyl group, an aryl group, a heteroaryl group or a pharmaceutically acceptable metal ion.

More preferred embodiments of the invention have the following formulae:

Compound 9

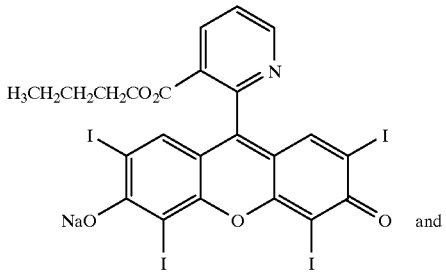
and

Compound 10

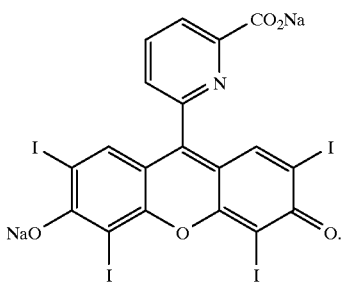

In another aspect the invention provides a method of antagonizing the interaction between IgE and FcεRI on a cell surface. The method comprises the step of contacting the cell with an IgE antagonizing amount of a compound having a tetracyclic skeleton of the formulae described above. More preferred compounds are designated as Compounds 1–8 described above.

In one preferred embodiment, the cell is within a mammal and the tetracyclic compound is administered to a mammal. In another preferred embodiment, the administration of the tetracyclic compound to a mammal is effective to alleviate the anaphylactic reactions. In another preferred embodiment, the administration of the tetracyclic compound is effective to inhibit the release of at least one allergy mediator from cells. In each of these embodiments, the tetracyclic compound may be administered topically, parenterally or orally.

As used herein, "alleviate" means to reduce the symptoms of a reaction or to otherwise inhibit or decrease a reaction.

In another embodiment, the tetracyclic compound is used in an in vitro diagnostic to measure antibodies against FcεRI α (anti-FcεRI α), for example in a fluid sample. Generally, the method includes measuring the quantity of anti-FcεRI α by mixing a fluid sample with a quantity of the receptor, FcεRI α, in the presence and absence of a tetracyclic compound, and measuring the quantity of anti-FcεRI α using a labelled antibody which specifically binds to a human Fc region. A comparison of the amount of anti-FcεRI α antibody found in the presence and absence of a tetracyclic compound is indicative of the quantity of anti-FcεRI α antibody in the sample.

DESCRIPTION OF THE PREFERRED EMBODIMENTS

Antagonizing the interaction between IgE and its high affinity receptor FcεRI would likely aid in reducing the allergic response in individuals sensitive to various allergens. Peptide analogs of IgE and/or anti-IgE antibodies can be used to inhibit interaction between IgE and FcεRI. Alternatively chemical molecules which antagonize the interaction between IgE and FcεRI can be identified.

It has been discovered that a class of compounds having a tetracyclic skeleton can antagonize the interaction between IgE and FcεRI. Thus, these tetracyclic compounds may be effective to alleviate the IgE-mediated immune responses leading to allergic symptoms. As used herein, the term "tetracyclic compound" generally refers to the tetracyclic compounds of this invention. The specific compounds useful to antagonize the interaction between IgE and FcεRI are described in more detail below.

Preparation of Tetracyclic Compounds

The tetracyclic compounds of this invention have the general formula:

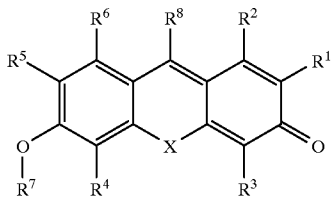

The atom or group represented by each of $R^1$, $R^2$, $R^3$, $R^4$, $R^5$, and $R^6$ is the same or different and is independently hydrogen, hydroxyl, nitro, cyano, isothiocyano, a halogen, a sulfo group, a phospho group, an alkyl group having 1 to 6 carbon atoms, an alkoxy group having 1 to 6 carbon atoms, an allyl group, an aryl group, a heteroaryl group, an alkylaryl group, an alkylheteroaryl group, an allylaryl group, an alkoxycarbonyl group having 1 to 6 carbon atoms, a carboxy group, an alkylcarbonyl group having 1 to 6 carbon atoms, an arylcarbonyl group or where appropriate, salts thereof.

The atom or group represented by each of $R^1$, $R^2$, $R^3$, $R^4$, $R^5$, and $R^6$ also independently can be an aminocarbonyl group, an alkylaminocarbonyl group having 1 to 6 carbon atoms, an arylaminocarbonyl group, a heteroarylaminocabonyl group, an acylamino group, an alkylamino group having 1 to 6 carbon atoms, a dialkylamino group, an arylamino group, an alkylurea group having 1 to 6 carbon atoms, an arylurea group or where appropriate, salts thereof, In addition, the atom or group represented by each of $R^1$, $R^2$, $R^3$, $R^5$, and $R^6$ independently can be an aklsulfonyl group having 1 to 6 carbons atoms, an arylsulfonyl group, an alkylsulfonylamino group having 1 to 6 carbon atoms, an arylsulfonylamino group or where appropriate, salts thereof.

The atoms and groups described above are typical substituents for molecules having a multiple ring system such as the tetracyclic compounds of this invention. Halogens include fluorine, chlorine, bromine and iodine. Alkyl groups having 1 to 6 carbons atoms are linear or branched alkyl groups that are readily known to those skilled in the art. More preferred alkyl groups include, but are not limited to, methyl, ethyl, n-propyl, isopropyl, n-butyl, sec-butyl and tert-butyl. Likewise, substituents that contain alkyl groups, such as an alkoxy group, include the above described embodiments. That is, preferred embodiments for alkoxy groups include, amongst others, methoxy, ethoxy, propoxy, isopropoxy, n-butoxy, sec-butoxy and tert-butoxy.

Aryl groups should be understood to encompass an aromatic ring structure with various substitution thereon. Various substitutions on the aryl group can result in structures having multiple rings. Heteroaryl groups refers to the basic aromatic ring structure with one or more carbon ring atoms replaced with one or more heteroatoms. If two or more heteroatoms are contained in one aryl group, the heteroatoms can be independently selected. Heteroatoms include, but are not limited to, oxygen, nitrogen and sulfur. As with aryl groups, various substitutions on the heteroaryl group can result in structures having multiple rings. The preferred aryl group is a phenyl group. The preferred heteroaryl group is pyridine. Similar to alkyl groups, substituents that contain aryl or heteroaryl groups, such as an arylcarbonyl group, include the above described embodiments.

The atom or group represent by $R^7$ is hydrogen, a pharmaceutically acceptable metal ion, an arylcarbonyl group or an alkylcarbonyl group having 1 to 6 carbon atoms. In addition to pharmaceutically acceptable metal ions, other entities that form a pharmaceutically acceptable salt of the tetracyclic compound can be used. Examples of preferred pharmaceutically acceptable salts include, amongst others, lithium, sodium and potassium.

The variable X is oxygen, sulfur or a secondary or tertiary nitrogen moiety having the formula $NR^9$, where $R^9$ is hydrogen or an alkyl group having 1 to 6 carbon atoms. In more preferred embodiments, the variable represented by X is oxygen. The group represented by $R^8$ is an aryl group or a heteroaryl group as described above. Since the variable $R^8$ is a cyclic entity, the four rings of the compounds of this invention become evident.

In preferred embodiments of the tetracyclic compound, the atom or group represented by $R^1$ and $R^6$ is hydrogen and the atom or group represented by $R^1$, $R^3$, $R^4$, and $R^5$ is hydrogen, hydroxyl, nitro, cyano or a halogen. In other preferred embodiments, the atom represented by $R^7$ is hydrogen or a pharmaceutically acceptable metal ion.

In one preferred embodiment, the group represented by $R^8$ has the formula:

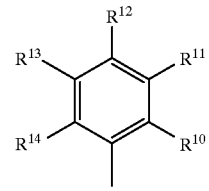

The atom or group represented by each of $R^{10}$, $R^{11}$, $R^{12}$, $R^{13}$ and $R^{14}$ is these or different and is independently hydrogen, a halogen, an alkyl group having 1 to 6 carbon atoms, an allyl group, an aryl group, an alklaryl group, an allylaryl group, a heteroaryl group, an alkylheteroaryl group, an alkoxycarbonyl group having 1 to 6 carbon atoms, an aryloxycarbonyl group, a carboxy group, a sulfo group, a phospho group, an alkylcarbonyl group having 1 to 6 carbon atoms, an arylcarbonyl group or where appropriate, salts thereof. The atom or group represented by each of $R^{10}$, $R^{11}$, $R^{12}$, $R^{13}$ and $R^{14}$ also can be an alkylsulfonyl group having 1 to 6 carbon atoms, an arylsulfonyl group, a sulfamoyl group, an alkylsulfamoyl group having 1 to 6 carbon atoms, an arylsulfamoyl group, an acylamino group having 1 to 6 carbon atoms or where appropriate, salts thereof.

In more preferred embodiments, the atom or group represented by $R^{10}$ is a carboxylic acid, a carboxylic ester or a pharmaceutically acceptable salt thereof. As such, the entity $R^{10}$ can be represented by the formula $-CO_2R^{15}$. Accordingly, $R^{15}$ is hydrogen, a linear or branched alkyl group, an allyl group, an aryl group, an alkylaryl group, an heteroaryl group, an alkylheteroaryl group, an allylaryl group or a pharmaceutically acceptable metal ion. In another more preferred embodiment, the atom or group represented by $R^{11}$, $R^{12}$, $R^{13}$ and R14 is independently hydrogen, a halogen, a carboxylic ester, a carboxylic acid or pharmaceutically acceptable salts thereof.

In another more preferred embodiment, the variables $R^1$ and $R^5$ are the same and $R^3$ and $R^4$ are the same. In yet another preferred embodiment, the variables $R^1$, $R^3$, $R^4$ and $R^5$ are all the same. Other more preferred embodiments have the atom or group represented by $R^{11}$, $R^{12}$, $R^{13}$ and $R^{14}$ independently being hydrogen or a halogen.

More preferred embodiments of the invention have the following formulae:

Compound 1

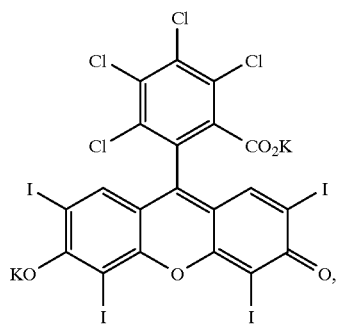

Compound 2

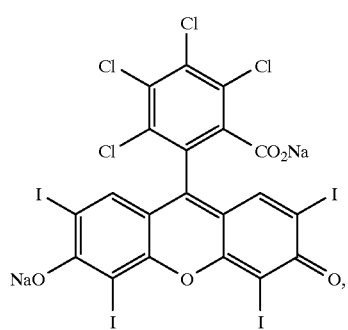

Compound 3

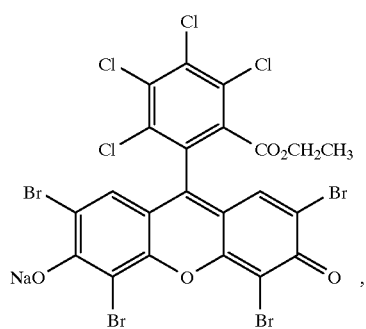

Compound 4

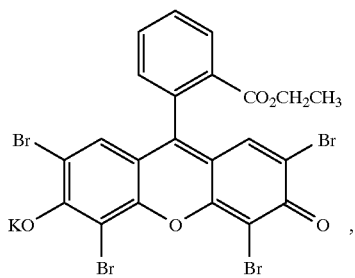

Compound 5

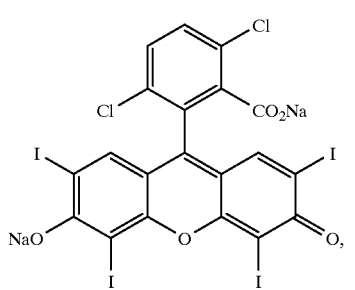

Compound 6

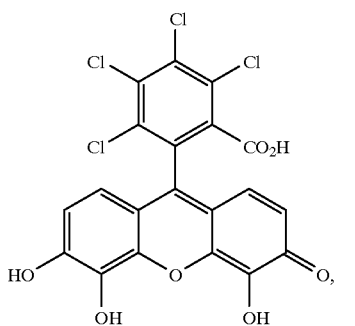

Compound 7

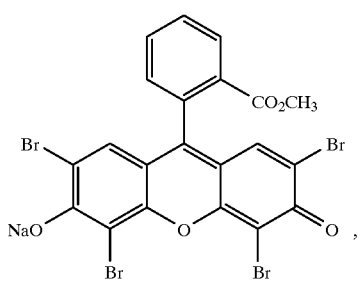

and

Compound 8

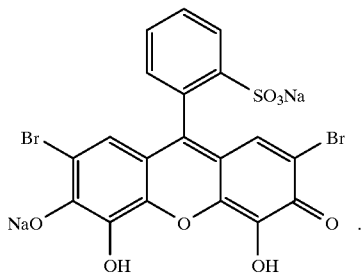

Other more preferred embodiments of this invention include, but are not limited to, compounds having the following formulae:

Compound 11

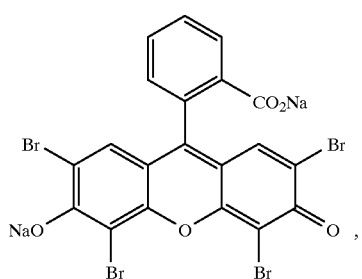

Compound 12

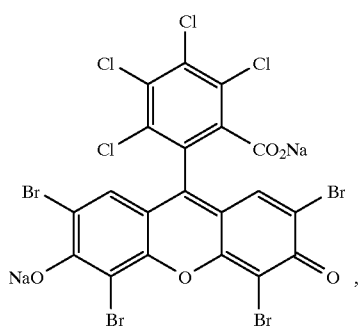

Compound 13

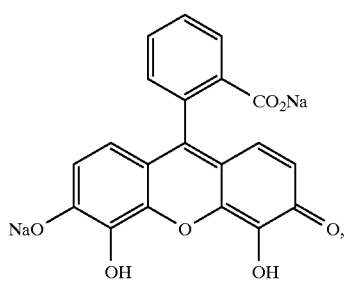

Compound 14

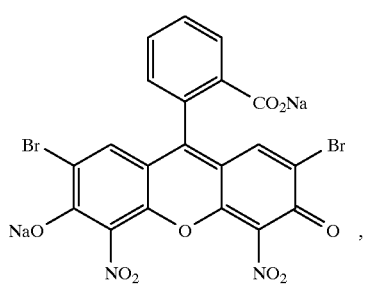

Compound 15

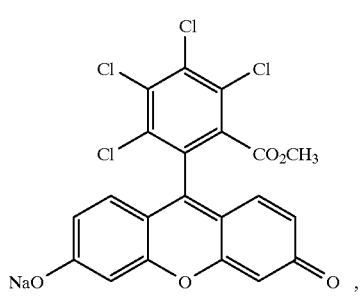

Compound 16

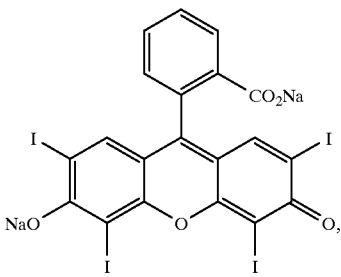

Compound 17

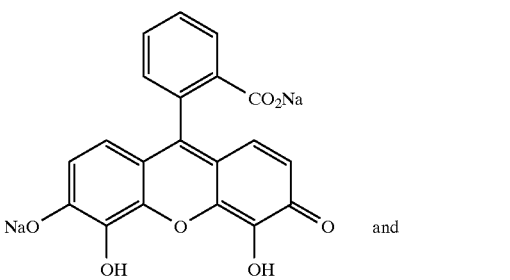

and

Compound 18

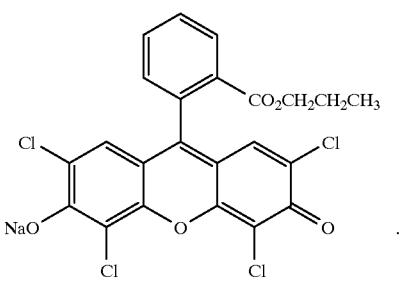

In another preferred embodiment, the group represented by $R^8$ has the formula:

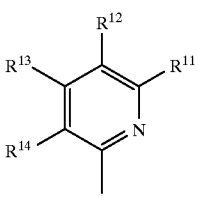

The atom or group represented by each of $R^{11}$, $R^{12}$, $R^{13}$ and $R^{14}$ is the same or different and is independently hydrogen, a halogen, an alkyl group having 1 to 6 carbon atoms, an allyl group, an aryl group, an alkylaryl group, an allylaryl group, a heteroaryl group, an alkylheteroaryl group, an alkoxycarbonyl group having 1 to 6 carbon atoms, an aryloxycarbonyl group, a carboxy group, a sulfo group, a phospho group, an alkylcarbonyl group having 1 to 6 carbon atoms, an arylcarbonyl group, an alkylsulfonyl group having 1 to 6 carbon atoms, an arylsulfonyl group, a sulfamoyl group, an alkylsulfamoyl group having 1 to 6 carbon atoms, an arylsulfamoyl group, an acylamino group having 1 to 6 carbon atoms or where appropriate, salts thereof.

In more preferred embodiments, the atom or group represented by $R^{11}$, $R^{12}$, $R^{13}$ and $R^{14}$ is independently hydrogen, a halogen, a carboxylic ester, a carboxylic acid or a pharmaceutically acceptable salt thereof. In another more preferred embodiment, the atom or group represented by $R^{11}$ or $R^{14}$ is the group —$CO_2R^{15}$ where $R^{15}$ represents hydrogen, a linear or branched alkyl group, an allyl group, an aryl group, an alkylaryl group, an allylaryl group, a heteroaryl group, an alkylheteroaryl group or a pharmaceutically acceptable metal ion.

More preferred embodiments of the invention have the following formula:

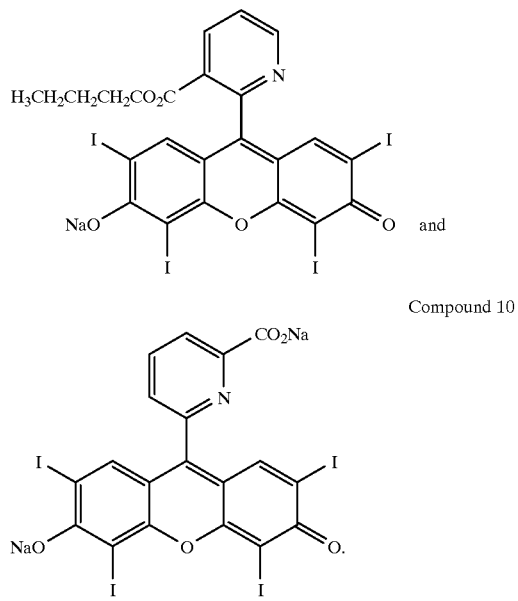

Compound 9 and

Compound 10

The tetracyclic compounds of this invention are commercially available from chemical suppliers or can be synthesized using standard synthetic techniques. Specific derivatives of tetracyclic compounds can be prepared according to chemical synthesis methods known in the art. See, for example, Orndorff et al., *J. Amer. Chem. Soc.*, 36:680–725 (1914); Tanaka, *Bull, Chem, Soc. Jpn.*, 3:288–289 (1928); Lamberts, et al., *J. Amer. Chem. Soc.*, 105:7465–7467 (1983); Zakrzewski et al., *Tetrahedron*, 43(20):4507–4512 (1987). These publications are herein incorporated by reference.

Amongst the various synthetic pathways to the tetracyclic compounds, a preferred synthetic method involves the condensation of a resorcinol moiety and a phthalic acid moiety. These moieties and derivatives thereof are commercially available or can be synthesized using methods known in the art. For example, condensation of resorcinol with tetrachlorophthalic acid produces a compound having the formula:

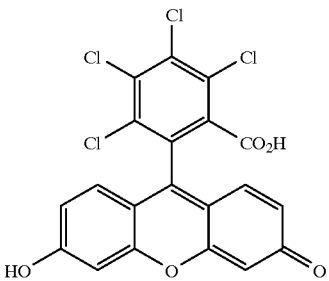

Compound 19

This condensation reaction typically is conducted at high temperature in the presence of a Lewis acid such as zinc oxide. Depending on the particular condensation product, appropriate reaction conditions and reagents are provided in the chemical literature or are known to those skilled in the art.

The condensation reaction described above produces tetracyclic compounds of this invention. The tetracyclic framework further can be manipulated to produce other embodiments of this invention. Other substituents typically are added to the tetracyclic framework by a variety of techniques. A specific example of a synthetic technique for introducing iodine atoms onto a tetracyclic compound involves treating the tetracyclic compound with a reagent such as iodine monochloride (ICl). In particular, treatment of Compound 19 with ICl in an organic acid produces, after isolation, a compound of the formula:

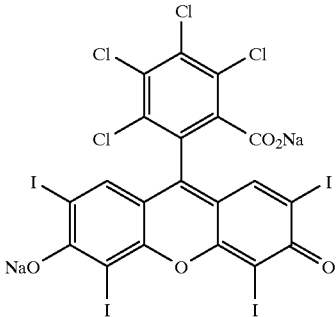

Compound 2

Although the product of the iodo addition reaction is depicted as its sodium salt, it should be understood that various salts of the tetracyclic compounds easily can be made depending upon the conditions under which the compound is isolated.

Other compounds of the invention can be produced by utilizing additional synthetic steps. Functionalities present on the tetracyclic skeleton can be further derivatized or substituted with other functionalities to create various substitution patterns. For example, following the formation of a tetracyclic compound having a free carboxylic acid moiety as shown in Compound 2 above, esterification of the acid produces the corresponding carboxylic ester. Esters that are useful in this invention include, but are not limited to, methyl, ethyl, n-propyl, isopropyl, n-butyl, sec-butyl and tert-butyl. In addition, esters formed by the addition of an aryl group, an allyl group, an alkylaryl group and an allylaryl group also are included amongst the carboxylic ester compounds of this invention. Other examples of preferred esters include, amongst others, benzyl ester and cinnamyl esters.

It also will be appreciated that tetracyclic compounds can be derived from spiro compounds having the general formula:

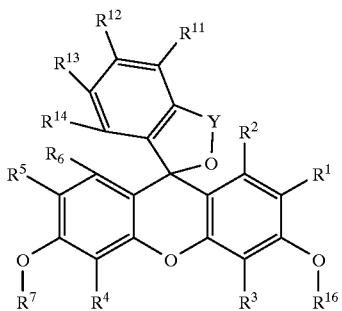

The variables $R^1$–$R^{14}$ previously described. The variable represented by Y can be a carbonyl group (C=O), a sulfoxide group (S=O), a sulfone group (O=S=O) or a phospho derivative (O=P—O). The atom or group represented by $R^{16}$ typically is the same as that for $R^7$.

Spiro compounds of the above general formula typically are stable at low pH. When in a solution having a near neutral pH or above, the five-member spiro compound will "open" to produce a tetracyclic compound. If the variable Y is a carbonyl group, the five-membered lactonic ring will "open" to form the general tetracyclic compounds of this invention with $R^{10}$ as a carboxylic acid. Those skilled in the art will realize that either before or after the ring opening, manipulation of the spiro compounds is possible as described above for tetracyclic compounds.

Efficacy Results

The members of the above described class of compounds antagonize the binding of IgE to FcεRI. As used herein, "antagonize" means to reduce, inhibit, or block the binding of IgE to its binding site upon the IgE receptor, FcεRI. The disclosure herein teaches those of ordinary skill in the art how to identify various individual compounds which effectively antagonize the IgE/FcεRI interaction sufficient to have significant therapeutic or diagnostic utility. The disclosure provided herein also teaches how to use compositions having activity that antagonizes the interaction between IgE and FcεRI.

A therapeutically effective amount of a compound of this invention is an amount of the individual agent of the class of substituted compounds having a tetracyclic skeleton such that the desired clinical endpoint, for example blocking the anaphylactic reaction, is reached. The amount to be administered is dependent on the potency, bioavailability, in vivo half-life, and toxicity of the individual compound. In general, the dose would reasonably be expected to range from 1 mg to 1 g per adult per administration.

Compounds which are particularly effective for each of the purposes include substituted derivatives of the tetracyclic compounds particularly described above. It should be understood that individual compounds of this invention as well as mixtures of two or more compounds are contemplated to be effective for each of the purposes described herein.

The language "therapeutically effective amount" is intended to include the amount of the tetracyclic compound sufficient to antagonize the interaction between IgE and FcεRI in the subject being treated. A therapeutically effective amount can be determined on an individual basis and will be based, at least in part, on consideration of the severity of the symptoms to be treated. Further, the effective amounts of the tetracyclic compound may vary according to age, sex, and weight of the subject being treated. Thus, a therapeutically effective amount of the tetracyclic compound can be determined by one of ordinary skill in the art employing such factors described above using no more than routine experimentation in clinical management.

A therapeutically effective amount of the tetracyclic compound comprises an amount of the tetracyclic compound such that the interaction between IgE and FcεRI is antagonized over the normal duration of therapy. The amount to be administered will depend upon the physical-chemical characteristics of the individual compounds, the route of administration, the bioavailability of the agents by the chosen route, and the potency of the individual agents to antagonize the interaction between IgE and FcεRI. The concentration of tetracyclic compound administered should be in a range sufficient to permit ready application of the formulation in an amount which delivers the desired amount of tetracyclic compound. In general, the dose reasonably would be expected to range from 1 mg to 1 g per adult human per administration for systemic use.

In the preferred embodiments of each aspect of the present invention involving clinical uses, the composition of the tetracyclic compound is prepared in a pharmaceutical acceptable carrier substance for oral ingestion or parental injection. The language "pharmaceutically acceptable carrier" is intended to include substances capable of being co-administered with the tetracyclic compound and which allows the compound to perform its intended function of antagonizing the interaction between IgE and FcεRI Examples of pharmaceutically acceptable carriers are commercially available inert gels or liquids. Gels comprise the tetracyclic compound, base selected from oleaginous base, water or emulsion-suspension base, and a gelling agent, such as hydroxypropyl cellulose, acrylic acid polymers, and the like. Liquid carriers include emulsions, solutions, and suspensions, for example, oils such a corn oil, buffers such as phosphate buffered saline, saline, ethanol, polyethylene glycol, glycerin, polypropylene glycol, dimethysulfoxide, dimethyacetamide. Liquids may include proteins such as albumin, a detergent such as Tween 80, and mono-, oligo- or polysaccharides such as glucose, lactose, cyclodextrins and starch. The term, "pharmaceutically acceptable salts" is intended to include salts which are recognized in the art, and may also be used for the preparation of tetracyclic compounds. Typically these salts are capable of being hydrolyzed under physiological conditions. Examples of such salts include sodium, potassium, and hemisulfate. Additionally, a carrier having effective bioavailability should be used in preparation of the compounds for oral ingestion.

The term "subject" is intended to include all mammals, such as humans, dogs, cats, horses, cows, goats, rats and mice.

Assessment of Antagonistic Activity of Tetracyclic Compounds

Compounds which antagonize the interaction of IgE and FcεRI can be readily identified using the assays described below. The described in vitro binding assays provide for the rapid screenings of large numbers of compounds for their ability to antagonize the interaction between IgE and FcεRI. The binding assay also may be automated using robotics. Compounds which inhibit IgE/FcεRI binding in the protein-based binding assay by approximately 80% or greater are considered efficient antagonists for the interaction between IgE and FcεRI. Compounds which are identified by the protein-based binding assay may be screened by the in vitro cell-based binding assay for confirmation. The binding assays may be automated.

A protein-based in vitro assay was developed to screen for compounds which block the interaction between IgE and FcεRI. This assay used human IgE and soluble FcεRI α proteins which were prepared as outlined below. As will be described more below, the assay was performed in the format of an Enzyme-linked ImmunoSorbent Assay (ELISA) as follows. ELISA plates were prepared by coating 96-well plates with soluble FcεRI α protein. In the binding step, biotinylated IgE was captured by the FcεRI α in the wells. In the detection step, bound biotinylated IgE was quantitated by the addition of avidin-horseradish peroxidase and a chromogenic substrate. For the screening of antagonists, the IgE and FcεRI binding assay was performed in the presence of various testing compounds. Compounds that inhibit the interaction between IgE and FcεRI α could be readily detected. This assay was then applied to screen tens of thousand of compounds from a diversified chemical library. Several compounds belonging to a class of tetracyclic compounds were discovered to inhibit the interaction between IgE and FcεRI α with a concentration that inhibits 50% of the binding ($IC_{50}$) of less than about 5 $\mu$g/ml. Furthermore, these compounds were shown to inhibit IgE and FcεRI α interaction in the cell-based binding assay.

Preparation and Purification of Human IgE

To provide IgE for the ELISA, a recombinant IgE DNA construct was built by ligating a mouse heavy chain variable region, Vh, gene fragment to a human IgE heavy chain, Cε. This construct was then transfected into the light chain producing myeloma J558L (Schwarzbaum, et al., Eur. J. Immunol., 1989, 9:1015–1023). The transfected cells produce IgE with a higher affinity for (4-hydroxy-3-iodo-5-nitrophenyl) acetic acid (NIP) than for (4-hydroxy-3-nitrophenyl) acetic acid (NP), and the recombinant IgE was purified using tis property in the following step.

The growth medium collected from the above transfected cell culture was concentrated 30–50 times by membrane filtration (Filtron, Northboro, Mass.) and passed through a column of NIP (Genosys Biotechnologies Inc.)-bovine serum albumin (BSA) sepharose. The bound IgE was subsequently eluted from NIP-BSA sepharose using 5 M $MgCl_2$. The eluate was then dialyzed in phosphate buffered saline (PBS). The integrity of the purified IgE was analyzed by SDS-polyacrylamide gel electrophoresis.

Preparation and Purification of Fc-FcεRI

To provide soluble FcεRI α protein for ELISA, a DNA construct was made to produce soluble FcεRI α as a protein fused to the Fc region of the human immunoglobulin G heavy chain. The protein product of the construct will he termed Fc-FcεRIα. The construction of the expression vector and the production of the fusion protein, termed an immunofusin, were previously described in Lo et al., U.S. patent application Ser. No. 08/305,700, herein incorporated by reference.

The culture media of the cells producing Fc-FcεRI α fusion protein was collected and passed through a Protein A Sepharose column (Repligen, Cambridge, Mass.). The bound fusion protein was eluted from the Protein A Sepharose in 100 mM sodium citrate buffer (pH 4.0) and immediately neutralized with 0.1 volume of 1M Tris-hydrochloride, pH 8. The integrity of the purified protein was analyzed by SDS-polyacrylamide gel electrophoresis.

Exemplary Assays for Identifying Compounds which Antagonize the IgE/FcεRI Interaction

EXAMPLE 1

Protein-based IgE-FcεRI Binding Assay

Fc-FcεRIα was diluted to 0.4 $\mu$g/ml in PBS and was used to coat 96-well plates. One hundred microliters of the FcεRIα fusion protein was added to wells of the 96-well plates, and the plate was incubated at 4° C. for 20 hr and washed twice with PBS/T (PBS containing 0.05% Tween-20). The non-specific binding sites in each of the wells were blocked with 200 $\mu$l of blocking buffer (PBS containing 1% of BSA and 1% of goat serum) at 37° C. for 2 hr. The plates were then washed 4 times with PBS/T and stored frozen at −20° C. The plates were thawed at room temperature just before use.

IgE was biotinylated as follows. Ten microliters of a 40 mg/ml sulfosuccimidyl 6-(biotinamido)-hexanolate (Pierce, Rockford, Ill.) in dimethylsulphoxide was added to 1 ml of 1 mg/ml IgE in sodium bicarbonate buffer, pH 8.0. After a 4 hr incubation at room temperature, the biotinylation was terminated by the addition of 25 $\mu$l of 2M Tris hydrochloride, pH 8 and the resulting biotinylated IgE was diayzed against PBS.

Compounds were screened for inhibition of IgE-FcεRIα binding as follows, using Compound X as an example. A solution of the biotinylated IgE and a Compound X was made in PBS so that the final concentration of biotinylated IgE was 0.4 $\mu$g/ml and that of Compound X was 10 $\mu$g/ml. One hundred microliter of this solution was added to wells of a 96-well plate which had been previously coated with Fc-FcεRIα. After a one-hour incubation, the plate was washed with PBS/T four times, and 100 $\mu$l of the solution of avidin-horseradish peroxidase (Avidin-HRP, Molecular Probe Inc., Eugene, Oreg.), at 0.25 $\mu$g/ml in PBS, was added to each well. After an additional one hour incubation at room temperature, the plate was again washed four times with PBS/T. The reaction with Avidin-HRP was developed by the addition of 100 $\mu$l of K-blue (Elisa Technologies, Lexington, Ky.) to each well. After an incubation at room temperature for 10 minutes, the reaction was stopped by the addition of 100 $\mu$l of stopping solution (Elisa Technologies, Lexington, Ky.) to each well. Absorption at 650 nm was measured using a Vmax kinetic microplate reader (Molecular Devices, Menlo Park, Calif.).

Compounds that inhibited IgE-FcεRI binding by greater than approximately 80% in the initial ELISA were selected. Potencies of the selected compounds to inhibit IgE-FcεRI binding were measured at different compound concentrations to determine their $IC_{50}$ values. It should be realized that a combination of two or more tetracyclic compounds of this invention may provide the appropriate activity as described herein. Table 2 shows the percent inhibitions at 10 $\mu$g/ml and the $IC_{50}$ of tetracyclic compounds identified in this invention, as well as other related compounds having the formulae:

Compound 1

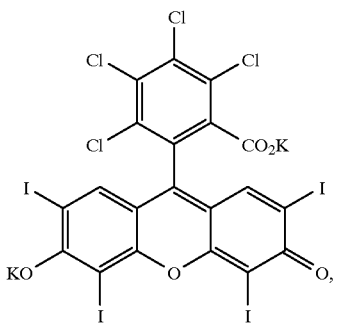

Compound 2

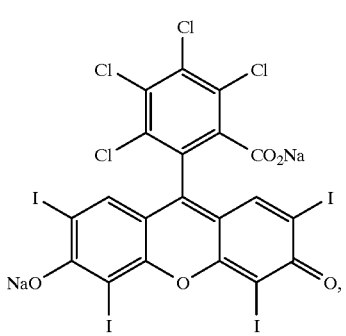

Compound 3

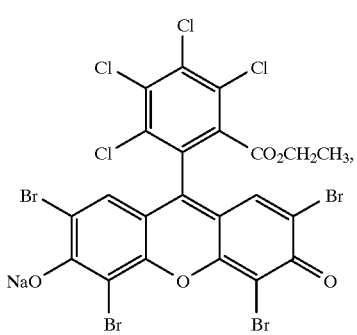

Compound 4

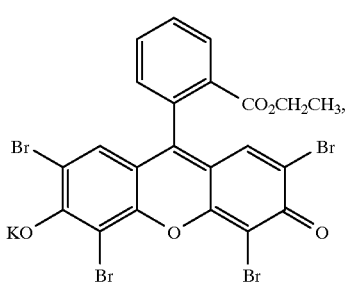

Compound 5

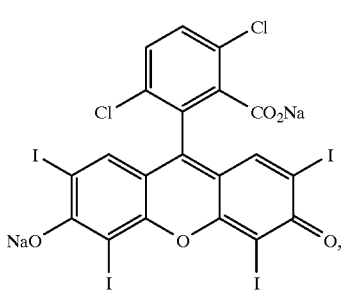

Compound 6

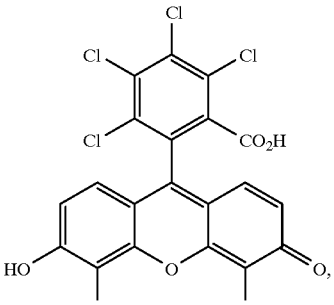

Compound 7

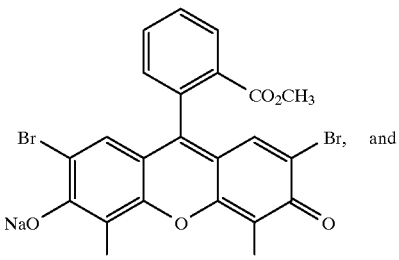

and

Compound 8

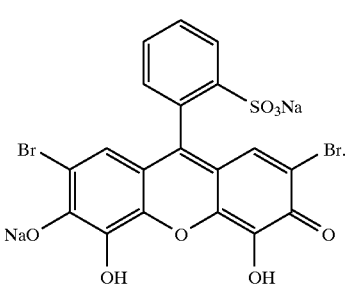

The compounds are listed according to the numerical designation described above.

TABLE 2

Inhibition of IgE/FcεRI Binding in Protein-based Assay

| Compound | % Inhibition at 10 μg/ml | $IC_{50}$ (μg/ml) |
| --- | --- | --- |
| 1 | 98 | 0.34 |
| 2 | 100 | 0.38 |
| 3 | 90 | 4.30 |
| 4 | 98 | 0.82 |
| 5 | 99 | 0.56 |
| 6 | 83 | 0.63 |
| 7 | 87 | 1.46 |
| 8 | 87 | 0.65 |

EXAMPLE 2

Cell-based IgE-FcεRI Binding Assay

Compounds initially identified as antagonists for IgE/FcεRI binding by the protein-based ELISA assay (see Example 1) were tested again in a cell-based binding assay using human FcεRI transfected rat basophil leukemia cell line, SX38. The cell culture was kept in minimum essential medium with Earle's salt (EMEM, GIBCO BRL, Life Technologies) in the presence of 16.7% fetal calf serum (FCS), 2 mM L-glutamine (GIBCO BRL, Life Technologies), 100 unit/ml penicillin, (GIBCO BRL, Life Technologies), 100 μg/ml streptomycin (GIBCO BRL, Life Technologies), and 1 mg/ml G418. About 1×10$^5$ cells in 50 μl of medium were seeded in the wells of 96-well flat bottom plates. After an overnight culture, plates were washed with PBS once and used in the following step, using Compound X as an example. A solution of biotinylated IgE and Compound X were made in PBS so that the final concentration of IgE was 1 μg/ml and that of Compound X was 10 μg/ml. Forty microliters of this solution was applied to each well and incubated at room temperature for two hours. The plates were washed three times with PBS, and 40 μl of avidin-horseradish peroxidase, at 1 μg/ml in PBS, was added to each well. After an additional hour of incubation at room temperature, the plate was again washed three times with PBS. The subsequent steps for the measurement of the bound IgE were performed as described in the protein-based IgE-FcεRI binding assay. Table 3 shows the IC$_{50}$ of the selected tetracyclic compounds identified in this invention and their percentage inhibition in the cell-based assay at 10 μg/ml.

TABLE 3

Inhibition of IgE-FcεRI Binding in Cell-based Assay

| Compound | % Inhibition at 10 μg/ml | IC$_{50}$ (μg/ml) |
| --- | --- | --- |
| 1 | 46 | 11.7 |
| 2 | 62 | 5.5 |
| 4 | 93 | 3.6 |
| 7 | 84 | 4.4 |

EXAMPLE 3

Antagonization of IgE/FcεRI Binding in an in situ Rat Passive Cutaneous Anaphylaxis (PCA) Model The tetracyclic compounds that antagonized the IgE and FcεRIα interaction identified in the protein-based assay were further evaluated in the rat PCA model (Haak-Frendscho, et al., J. Immunol., 151:351–358, 1993). This rat model was intended to demonstrate that the identified class of tetracyclic compounds will inhibit the binding between IgE and FcεRI in living animals, as evidenced by reduced anaphylaxis in the rat skin. Mouse anti-dinitrophenyl IgE (Sigma ImmunoChemicals, St. Louis, Mo.) is a bifunctional antibody which binds to dinitrophenyl as well as FcεRI. Exposure of anti-dinitrophenyl-IgE to dinitrophenyl-albumin causes aggregation of the antibody and induces the IgE mediated immune response. A concentration of 0.03 μg/ml mouse anti-dinitrophenyl-IgE in PBS was mixed with individual tetracyclic compounds at different concentrations. Fifty microliters of these solutions were injected into the skin of the shaved back of Sprague Dawley rats (Taconic, Germantown, N.Y.). As a positive control, the same amount of anti-dinitrophenyl-IgE in the absence of a tetracyclic compound was injected into the skin of the same rat at a different site. After a period of two hours the sensitized rats were challenged with an intravenous injection of 1 mg/ml of dinitrophenyl-human albumin (Sigma ImmunoChemicals, St. Louis, Mo.) in 1% Evan's blue dye. Thirty minute later, the rats were killed and skinned. Percent inhibition was calculated by the reduction of blue dye at the tetracyclic compound treated injection sites versus the positive control sites. An example of the inhibitory effect of compound 1 is shown in Table 4.

TABLE 4

Percent Inhibition of PCA Reaction by Compound 1.

| Concentration (μg/ml) | % Inhibition |
| --- | --- |
| 1 | 100% |
| 0.5 | 66% |
| 0.25 | 5% |

The Inhibition of PCA by selected tetracyclic compounds are shown in Table 5.

TABLE 5

Inhibition of anaphylaxis in the rat PCA model

| Compound | IC$_{50}$ (μg/ml) |
| --- | --- |
| 1 | 0.46 |
| 2 | 1.10 |
| 4 | 2.90 |

EXAMPLE 4

Antagonization of IgE/FcεRI Interaction in Systemic PCA Model

The compounds that have activity in the in situ PCA model were tested in the systemic PCA model. This model measures usefulness of a tetracyclic compound for blocking PCA in rats when the tetracyclic compound is administered systemically and the rats were sensitized with IgE at the skin. In this example, compound I was administrate first into the rats by intravenous (I.V.) injection, and immediately thereafter 0.03 μg/ml of anti-dinitrophenyl/IgE was injected into the skin of the shaved back of Sprague Dawley rats. After a sensitization period of 1 hr, the sensitized rats were challenged with an intravenous injection of 1 mg/ml of dinitrophenyl human albumin in 1% Evan's blue dye. Thirty minutes later, the rats were killed and skinned. As a positive control, PBS, lacking a tetracyclic compound, was administered by I.V. injection into Sprague Dawley rats, and the rats were treated in the same manner as the test rats. Percent inhibition of PCA obtained in this model is calculated by determining reduction of blue dye extracted from the tetracyclic compound treated rats compared to the positive control rats. The dose dependent inhibition of PCA by compound 1 in this model is shown in Table 6.

TABLE 6

PCA Inhibition of Compound 1 in Systemic CA Model

| Conc. (mg/kg) | % Inhibiton |
| --- | --- |
| 47 | 2.0% |
| 70 | 64.0% |
| 94 | 104.0% |
| 114 | 102.0% |

EXAMPLE 5

Toxicity Studies in Mice

The potential toxic side effects following systemic administration was investigated by administering compound 1 in PBS to mice in single I.V. injection. The data is shown in Table 7.

TABLE 7

Systemic Toxicity of Tetracyclic Compounds

| Compound | Dose (mg/kg) | No. of Mice | Route | No. of Death | $LD_{50}$ |
|---|---|---|---|---|---|
| 1 | 400 | 3 | I.V. | 0 | >400 mg/kg |

EXAMPLE 6

Pharmacokinetic Studies in Rats

The pharmacokinetic (PK) profile of the compounds following systemic I.V. injection was measured. Compound 1 was formulated in PBS and given to a rat at 10 mg/kg. Blood was drawn from the rat at different time points after injection. The concentrations of compound 1 in the blood were measured by HPLC after separation from serum. Table 8 shows a PK profile of compound 1.

TABLE 8

Pharmacokinetic Profile of Compound 1

| Time (minute) | Concentration (µg/ml) |
|---|---|
| 0 | 83 |
| 15 | 2.51 |
| 30 | 0.902 |
| 60 | 0.72 |
| 120 | 0.625 |
| 240 | 0.512 |

EXAMPLE 7

Hexosaminidase Release Assay

Tetracyclic Compounds that antagonized the IgE and FcεRIα interaction identified in the protein-based assay and cell-based assay were further evaluated in a screening assay using rat basophil leukemia cells (RBL cells). This assay is intended to demonstrate that the identified class of tetracyclic compounds will inhibit the IgE-mediated release of allergy mediators from RBL cells, as evidenced by reduced levels of hexosaminidase which is released concurrently with histamine and other allergy mediators. About $2\times10^5$ RBL cells were seeded per well in a 96 well plate and were incubated overnight at 37° C. A mixture of biotinylated mouse IgE (100 µl of 0.125 µg/ml) and a tetracyclic compound, e.g. compound 2, in medium was added lo each well and was incubated for 1 hour at 37° C. The cells were then washed twice with triggering buffer (119 mM NaCl, 5 mM KCl, 25 mM disodium PIPES, 5.6 mM glucose, 1 mM $CaCl_2$, 0.1% BSA), and pre-incubated in triggering buffer for 10 min. at 37° C. One hundred microliters of 0.02 µg/ml streptavidin in triggering buffer was then added and the cells were incubated for an additional 30 min. at 37° C. The 96 well plate is then centrifuged at 4° C. to pellet all cells, and 80 µl of the supernatant is harvested on ice and transferred to another 96 well plate. As a positive control, two aliquots of about $2\times10^5$ RBL cells were lysed with 100 µl of 0.2% Triton in triggering buffer, and the supernatant was harvested after centrifugation to pellet all cell debris. Addition of streptavidin to RBL cells, which have been incubated with biotinylated IgE will trigger the release of IgE mediated allergy mediators, such as histamine. Antagonization of IgE/FcεRI binding by a tetracyclic compound results in the release of a reduced level of allergy mediators. The release of allergy mediators was quantitated by assaying for the presence of the enzyme hexosaminidase in the supernatant The concentration of hexosaminidase was determined by hydrolysis of its substrate, p-NAG (p-nitrophenyl-N-acetate-ε-D-Glucosaminidase, Sigma Chemical Co.) in citrate buffer (pH 4.5) at 37° C. for 1 hr.

Table 9 shows the percent inhibition of IgE mediated release of hexosaminidase by compound 2 at several concentrations.

TABLE 9

Percent Inhibition of IgE Mediated Hexosaminidase Release by Compound 2

| Concentration (µg/ml) | % Inhibition |
|---|---|
| 0.1 | 11% |
| 0.62 | 19% |
| 1.25 | 75% |
| 2.5 | 96% |
| 5 | 94% |

EXAMPLE 8

In vitro Diagnostic for FcεRI Antibodies

The presence of an antibody of the IgG class to the receptor FcεRI α, an anti-FcεRI α antibody, may be, responsible for chronic urticaria. The detection of anti-FcεRI α antibodies from a fluid sample will allow the identification of persons who are predisposed to allergy.

Recombinant mouse Fc- human FcεRI α is used to coat 96 well plates, and non-specific binding sites are blocked, as described above in example, 1. A serum sample is taken from an individual and is tested for presence of antibody directed against FcεRI α as follows. Successive dilutions of the serum sample are made in PBS so that a range of potential antibody concentrations may be tested. A tetracyclic compound is added to a parallel series of dilutions of the serum sample at a concentration which has been previously determined to inhibit 100% of IgE binding to the receptor. One hundred microliters of the sample solution either with or without tetracyclic compound are added to the wells of the 96 well plate which has previously been coated with Fc-FcεRI α. After a one-hour incubation, the plate is washed with PBS/T four times, and 100 µl of solution containing horseradish peroxidase-labeled antibody against the human Fc region, the heavy chain constant region or the light chain constant region is added (Jackson Immuno Research Laboratories Inc., West Grove, Pa.). Anti-human constant region antibodies labeled with other suitable labels, such as color labels, fluorescence labels or radioactive labels, may also be used. After an additional one hour incubation at room temperature, the plate is again washed four times with PBS/T. The reaction with horseradish peroxidase is developed by the addition of 100 µl of K-blue to each well. After an incubation at room temperature for 10 minutes, the reaction is stopped by the addition of 100 µl of stopping solution to each well. The absorption at 650 nm is read.

Samples containing antibody against the IgE binding site of FcαRI α will be determined by the blue staining of the wells in the absence of tetracyclic compound and the lack of blue staining of the well in the presence of tetracyclic compound. Sample which do not contain antibodies against FcεRI α will be determined by the lack of blue staining in both the presence and absence of tetracyclic compound. Samples containing antibodies against FcεRI α which do not bind at the IgE binding site will be determined by the presence of blue staining in the wells in both the presence and absence of tetracyclic compound.

Other embodiments of the invention will be apparent to those skilled in the art from a consideration of this specification or practice of the invention herein disclosed. It is intended that the specification be construed as exemplary only, with the true scope and spirit of the invention represented by the following claims.

We claim:
1. A method of antagonizing the interaction between IgE and FcεRI on a surface of a mammalian cell bearing FcεRI comprising the step of contacting the cell with an IgE antagonizing amount of a compound having the formula:

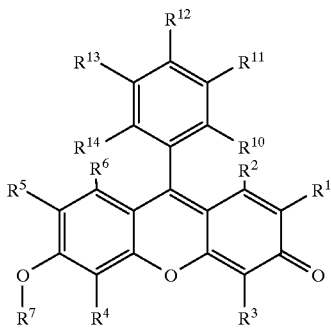

wherein the atom or group represented by each of $R^1$, $R^2$, $R^3$, $R^4$, $R^5$, and $R^6$ is the same or different and is independently selected from the group consisting of hydrogen, hydroxyl, and a halogen;

$R^7$ is hydrogen, a pharmaceutically acceptable metal ion, an arylcarbonyl group or an alkylcarbonyl group having 1 to 6 carbon atoms;

wherein the atom or group represented by each of $R^{11}$, $R^{12}$, $R^{13}$, and $R^{14}$ is the same or different and is independently selected from the group consisting of hydrogen, and a halogen; and $R^{10}$ is independently selected from the group consisting of an alkyl group having 1 to 6 carbon atoms, an alkoxy group having 1 to 6 carbon atoms, an alkoxycarbonyl group having 1 to 6 carbon atoms, a carboxy group, an alkylcarbonyl group having 1 to 6 carbon atoms, an alkylsulfonyl group having 1 to 6 carbons atoms, sulfo; and salts thereof.

2. The method of claim 1 wherein said cell comprises a population of cells in a sample derived from a mammal.

3. The method of claim 1 wherein said contacting step comprises administering said compound to a mammal.

4. The method of claim 3 comprising administering an amount of compound sufficient to inhibit induction of anaphylactic reactions.

5. The method of claim 3 comprising administering an amount of compound sufficient to inhibit release of allergy mediators.

6. The method of claim 3 wherein said administration step is conducted parenterally, topically or orally.

7. The method of claim 1, wherein said compound has the formula:

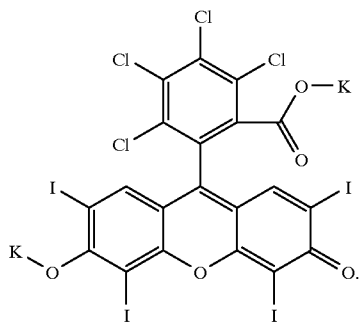

8. The method of claim 1, wherein said compound has the formula:

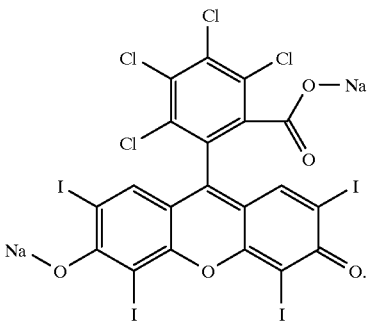

9. The method of claim 1, wherein said compound has the formula:

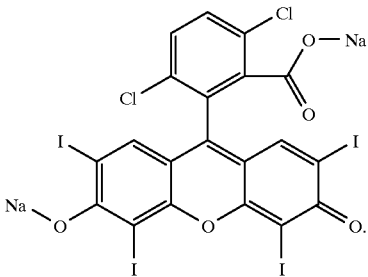

10. The method of claim 1, wherein said compound has the formula:

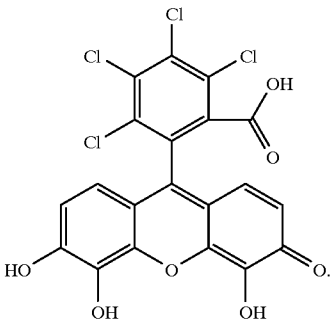

11. The method of claim 1, wherein said compound has the formula:

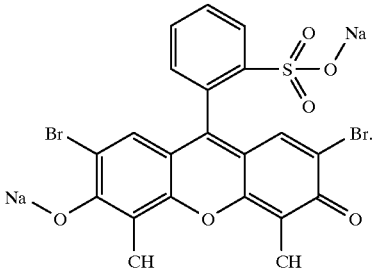

12. The method of claim 1, wherein said compound has the formula:

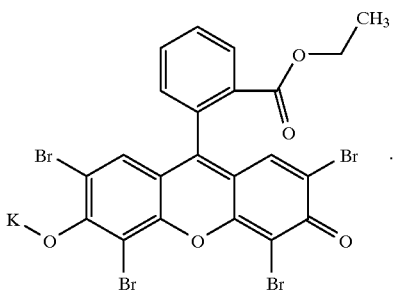

13. The method of claim 1, wherein said compound has the formula:

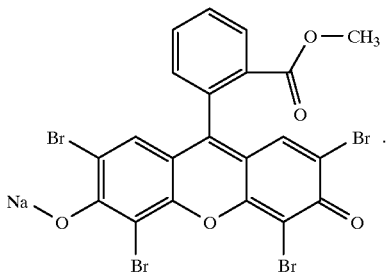

14. The method of claim 1, wherein said compound has the formula:

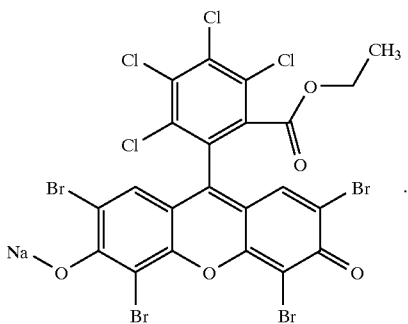

15. A method of antagonizing the interaction between IgE and FcεRI in vitro comprising the step of contacting said IgE and FcεRI with an IgE antagonizing amount of a compound having the formula:

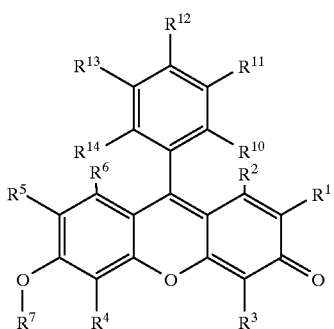

wherein the atom or group represented by each of $R^1$, $R^2$, $R^3$, $R^4$, $R^5$, $R^6$, $R^{10}$, $R^{11}$, $R^{12}$, $R^{13}$, and $R^{14}$ is the same or different and is independently selected from the group consisting of hydrogen, hydroxyl, nitro, cyano, isothiocyano, a halogen, a sulfo group, a phospho group, an alkyl group having 1 to 6 carbon atoms, an alkoxy group having 1 to 6 carbon atoms, an alkoxycarbonyl group having 1 to 6 carbon atoms, a carboxy group, an alkylcarbonyl group having 1 to 6 carbon atoms, an aminocarbonyl group, an alkylaminocarbonyl group having 1 to 6 carbon atoms, an acylamino group, an alkylamino group having 1 to 6 carbon atoms, a dialkylamino group, an alkylurea group having 1 to 6 carbon atoms, an alkylsulfonyl group having 1 to 6 carbons atoms, an alkylsulfonylamino group having 1 to 6 carbon atoms, and salts thereof; and $R^7$ is hydrogen, a pharmaceutically acceptable metal ion, an arylcarbonyl group or an alkylcarbonyl group having 1 to 6 carbon atoms.

16. The method of claim 15, wherein said FcεRI is on a surface of a mammalian cell.

17. The method of claim 15, wherein said compound has the formula:

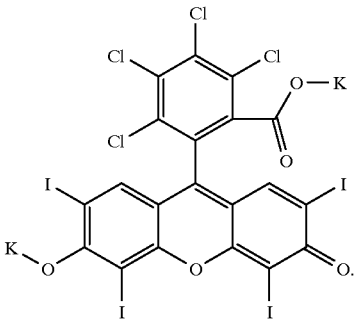

18. The method of claim 15, wherein said compound has the formula:

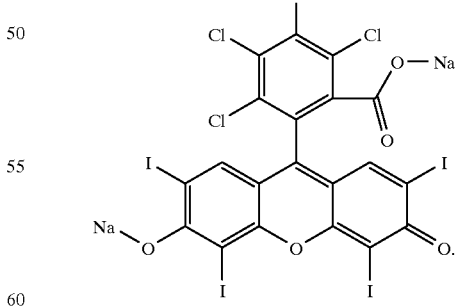

19. The method of claim 15, wherein said compound has the formula:

20. The method of claim 15, wherein said compound has the formula:
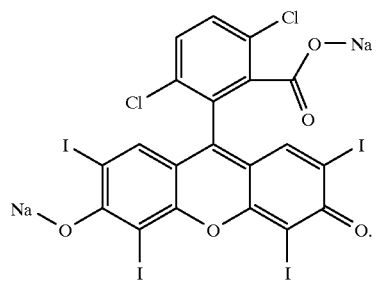
21. The method of claim 15, wherein said compound has the formula:
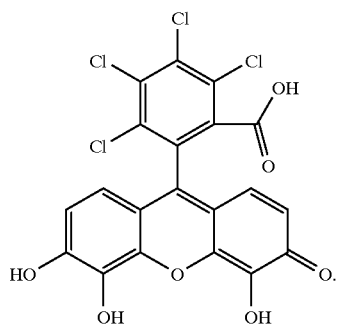
22. The method of claim 15, wherein said compound has the formula:
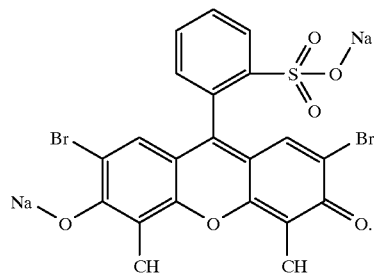
23. The method of claim 15, wherein said compound has the formula:
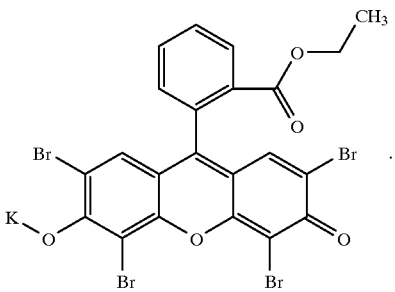
24. The method of claim 15, wherein said compound has the formula:
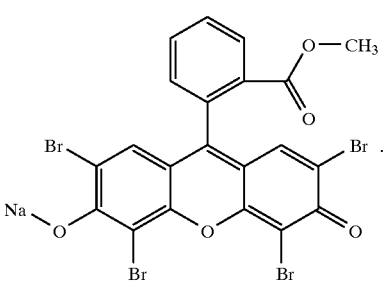
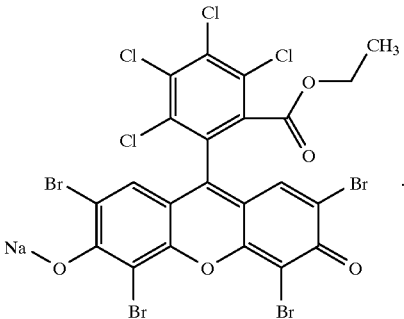
* * * * *

UNITED STATES PATENT AND TRADEMARK OFFICE
CERTIFICATE OF CORRECTION

PATENT NO. : 5,965,605
DATED : Oct. 12, 1999
INVENTOR(S) : Y.. Edmond Cheng et al It is certified that error appears in the above-identified patent and that said Letters Patent is hereby corrected as shown below:

On the title page: Item [54] and Column 1, line 3, please add "OF" to the title as follows:

INHIBITION OF THE BINDING OF HUMAN IGE TO ITS RECEPTOR BY TETRACYCLIC COMPOUNDS FOR THE ALLEVIATION OF IGE-MEDIATED IMMUNE RESPONSE

Abstract, item [57], line 5, please delete "module" and insert therefor --modulate--

Signed and Sealed this

Twentieth Day of June, 2000

*Attest:*

Q. TODD DICKINSON

*Attesting Officer*     *Director of Patents and Trademarks*